United States Patent
Qian et al.

(10) Patent No.: US 9,591,855 B2
(45) Date of Patent: Mar. 14, 2017

(54) DIINDOL-3-YLMETHANES AS POTENT NON-TOXIC ANTIFOULING COMPOUNDS

(71) Applicant: Hong Kong University of Science and Technology, Hong Kong (CN)

(72) Inventors: Peiyuan Qian, Hong Kong (CN); Ying Xu, Hong Kong (CN); Kailing Wang, Hong Kong (CN); Changyun Wang, Qingdao (CN)

(73) Assignees: THE HONG KONG UNIVERSITY OF SCIENCE AND TECHNOLOGY, Hong Kong (CN); CHINA OCEAN MINERAL RESOURCES R&D ASSOCIATION, Beijing (CN)

( * ) Notice: Subject to any disclaimer, the term of this patent is extended or adjusted under 35 U.S.C. 154(b) by 0 days.

(21) Appl. No.: 14/815,390

(22) Filed: Jul. 31, 2015

(65) Prior Publication Data
US 2016/0037773 A1   Feb. 11, 2016

Related U.S. Application Data

(60) Provisional application No. 61/999,833, filed on Aug. 7, 2014.

(51) Int. Cl.
*A01N 43/38* (2006.01)
*A01N 43/42* (2006.01)
*C08K 5/3417* (2006.01)
*C09D 5/16* (2006.01)

(52) U.S. Cl.
CPC ............ *A01N 43/38* (2013.01); *A01N 43/42* (2013.01); *C08K 5/3417* (2013.01); *C09D 5/1625* (2013.01)

(58) Field of Classification Search
CPC ...... A01N 43/38; A01N 43/42; C08K 5/3417; C09D 5/1625
USPC ........................................................ 514/314
See application file for complete search history.

(56) References Cited

PUBLICATIONS

Salta et al., Conference paper 2009. https://www.researchgate.net/publication/235901375.*
Fusetani Nat. Prod. Rep., 2011, 28, 400.*
Bell et al. Journal of Natural Products, 1994, 57(11) 1587-1590.*

* cited by examiner

*Primary Examiner* — Yevegeny Valenrod
(74) *Attorney, Agent, or Firm* — Saliwanchik, Lloyd & Eisenschenk

(57) ABSTRACT

The present invention provides high potency 3,3'-diindolylmethane (DIM) and analogue compounds as antifouling agents. The present invention further provides methods of preventing or reducing settlement and/or fouling of marine fouling organisms on surfaces of submerged objects by coating the surfaces with the 3,3'-diindolylmethane (DIM) and analogue compounds provided.

7 Claims, 4 Drawing Sheets

DIINDOL-3-YLMETHANES AS POTENT NON-TOXIC ANTIFOULING COMPOUNDS

BACKGROUND OF THE INVENTION

Marine biofouling refers to the undesirable colonization of microorganisms, algae, and animals on artificial surfaces immersed in seawater and also causes bio-corrosion for commercially important marine structures. The settlement and accumulation of biofoulers such as barnacles, bryozoans, and mussels on submerged substrates are a worldwide problem in marine systems and create massive technical and economic challenges for maritime industries, marine aquaculture, and cooling systems of power plants (Callow and Callow, 2002; Qian et al. 2007; Sievers et al. 2013)). For instance, large numbers of fouling organisms on ship hulls result in potential speed reduction and loss of maneuverability, thereby severely increasing fuel consumption of navigation (Yebra et al., 2004). The estimated annual cost of biofouling organisms is over $6.5 billion (Bhadury and Wright, 2004). In addition to huge material and economic losses in marine operations, fouling organisms on ship hulls also generate a series of environmental problems such as the invasion of non-native species (Davidson et al. 2009).

In the past, marine antifouling paints, mainly based on toxic heavy metal biocides (eg copper, lead, arsenic, cadmium), were widely used to control biofoulers. Organotins such as tributyitin (TBT) have been the most effective antifouling agents for several decades. However, an uneasy concealed danger behind the efficiency of these booster biocides is the acute toxicity to some non-target marine organisms even in the ng $1^{-1}$ range (Alzieu, 2000). The application of coatings containing organotins to ships has been totally banned by the International Maritime Organization (IMO) and Marine Environmental Protection Committee (MEPC) since 2008 (low Callow and Callow, 2011; Li et al., 2013)). Unfortunately, the alternatives to TBT that are currently used in market either contain copper, or Irgarol 1051, diuron, zinc pyrithione, chlorothalonil, and Sea-Nine 211 and can also have deleterious effect effects on ocean environment (Bellas, 2006; Thomas and Brooks, 2010). Therefore, the exploitation of effective and environmentally benign antifouling compounds is becoming an urgent requirement for marine coating industries.

To identify nontoxic and effective antifouling substances, active natural products have been extracted from marine sessile organisms such as corals, sea squirts and sponges (see reviews by Faulkner (2000) and Fusetani (2004)). However, in most instances, the yields of the active compounds by these marine organisms were too low to be developed into antifouling agents. To overcome this problem, much attention has been paid to the large-scale fermentation of microorganisms in recent years (see reviews by Fusetani (2011) and Qian et al. (2010, 2015).

BRIEF SUMMARY OF THE INVENTION

The present invention provides 3,3'-diindolylmethane (DIM) and analogue compounds as antifouling agents. DIM and several analogues from the bacterium *Pseudovibrio denitrificans* UST4-50 isolated from the Red Sea were isolated and their antifouling activities against the barnacle *Balanus* (=*Amphibalanus*) *amphitrite* and bryozoan *Bugula neritina* were tested. The structure-activity relationship of these metabolites and the acetylated derivative (4-(di(1H-indol-3-yl)methyl) phenyl acetate, DIM-Ph-4-OAc) of 4-hydroxyphenyl-3,3'-diindolylmethane (DIM-Ph-4-OH) were analyzed. DIM and DIM-Ph-4-OH were utilized to assess their toxicity against larvae of fouling organisms, and antifouling efficacy of marine coating containing DIM in marine environment.

In one aspect, the present invention provides methods of preventing or reducing settlement and/or fouling of marine fouling organisms on a surface of a submerged object, comprising:

obtaining a composition comprising one or more compounds represented by formula I:

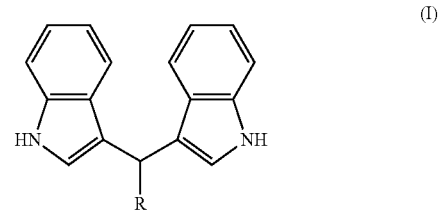

(I)

wherein R is selected from H, $CH_3$, $CHOHCH_2$, $C_8H_7N$, $COC_8H_7N$, $C_9H_6N$, Ph, Ph-4-OH, and Ph-4-OAc; and applying an effective amount of the composition to the surface, whereby settlement and/or fouling of marine fouling organisms on the surface is prevented or reduced.

In some embodiments, the compounds comprise one or more compounds represented by formulas II-X:

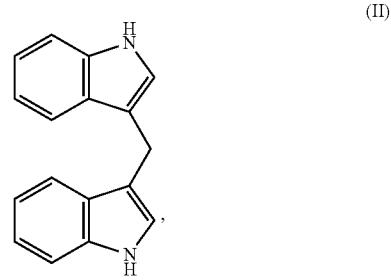

(II)

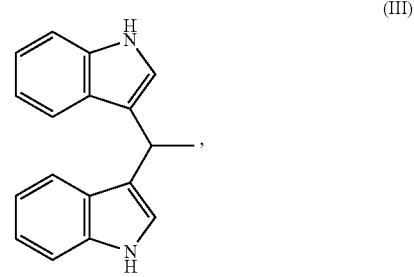

(III)

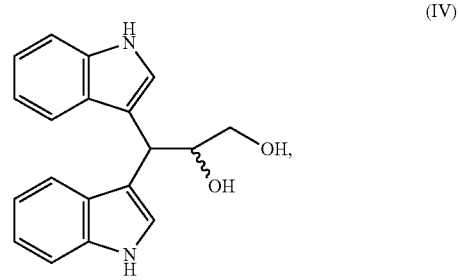

(IV)

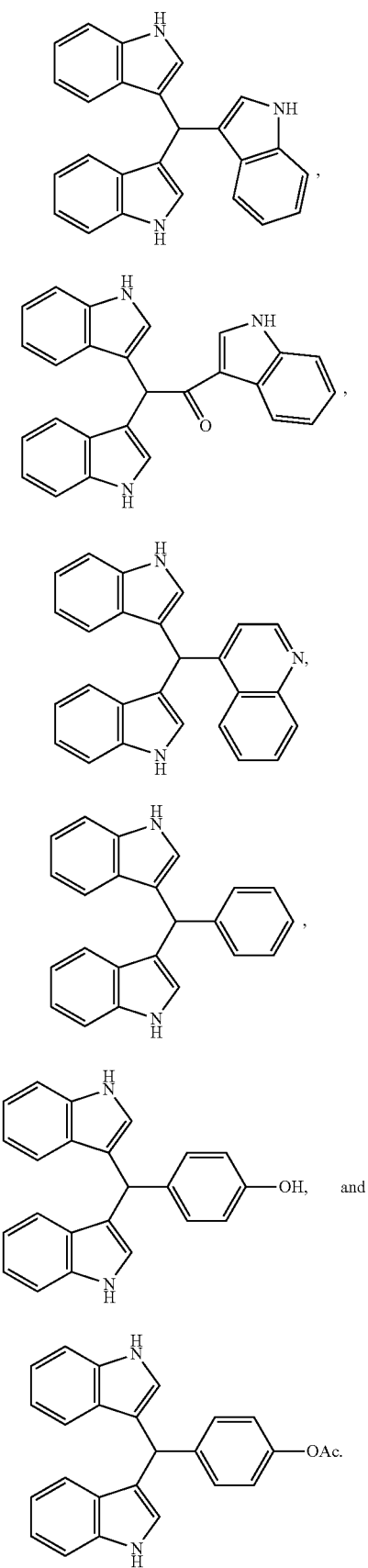

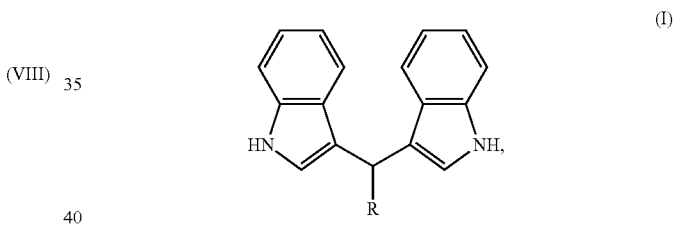

In some embodiments, the one or more compounds represented by formulas II-X exist in an extract of *Pseudovibrio denitrificans* UST4-50.

In some embodiments, the one or more compounds can be blended as antifouling components into film-forming components, and are therefore collectively made into an antifouling coating which can be used to inhibit the settlement and/or fouling of marine fouling organisms on the surface of a submerged object that is coated with the antifouling coating. The film-forming components can include, but are not limited to, the components known in antifouling paints used for preventing marine biofouling. These film-forming components may include components as recognized by those skilled in the art, such as but not limited to, one or more hydrolysable, soluble or insoluble resins. For example, the resins can be one or more of glyptal resin, acrylic resin, chlorinated rubber resin, epoxy resin, silicone resin, polyester resin, polyurethane resin, fluoropolymer resin, and other resins known to those skilled in the art. The film-forming components can be components of paint, such as a marine paint.

In another aspect, the present invention provides antifouling coatings, for reducing settlement and/or fouling of marine fouling organisms on a surface of a submerged object, comprising film-forming components and antifouling components; wherein the film-forming components comprise one or more resin; and wherein the antifouling components comprise one or more of the compounds represented by formula I:

(I)

wherein R is selected from H, $CH_3$, $CHOHCH_2$, $C_8H_7N$, $COC_8H_7N$, $C_9H_6N$, Ph, Ph-4-OH, and Ph-4-OAc.

In another aspect, the present invention provides methods for preventing or reducing settlement and/or fouling of marine fouling organisms on a surface of a submerged object, comprising painting the surface of the submerged object with antifouling coatings as provided herein.

The marine fouling organisms in which the methods and compounds of the present invention are useful against include, but are not limited to, one or more of barnacles, tubeworms, and bryozoans.

μM) and DIM-Ph-4-OH (8) (73.93 μM) that inhibited 100% of cyprid settlement of *Amphibalanus amphitrite*. After 24 hr of exposure, the cyprids were transferred to fresh seawater (FSW) and kept in incubator for 48 hr. In the control group, cyprids were kept in FSW without biocides during the course of the experiment. Values presented here were mean±SD (n=3) of the settled and unsettled (swimming) living larvae.

Figure 3:
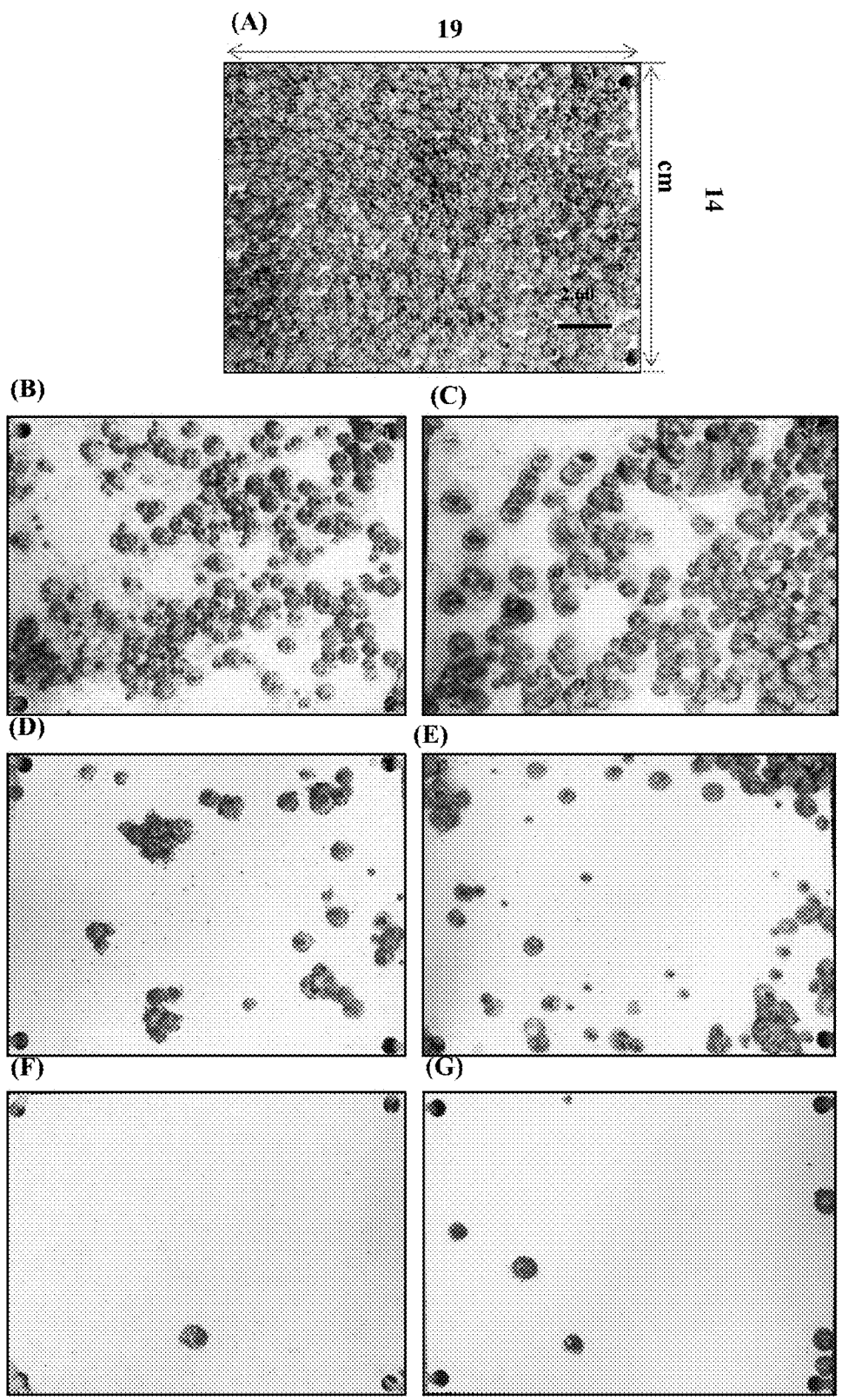
Figure 4:
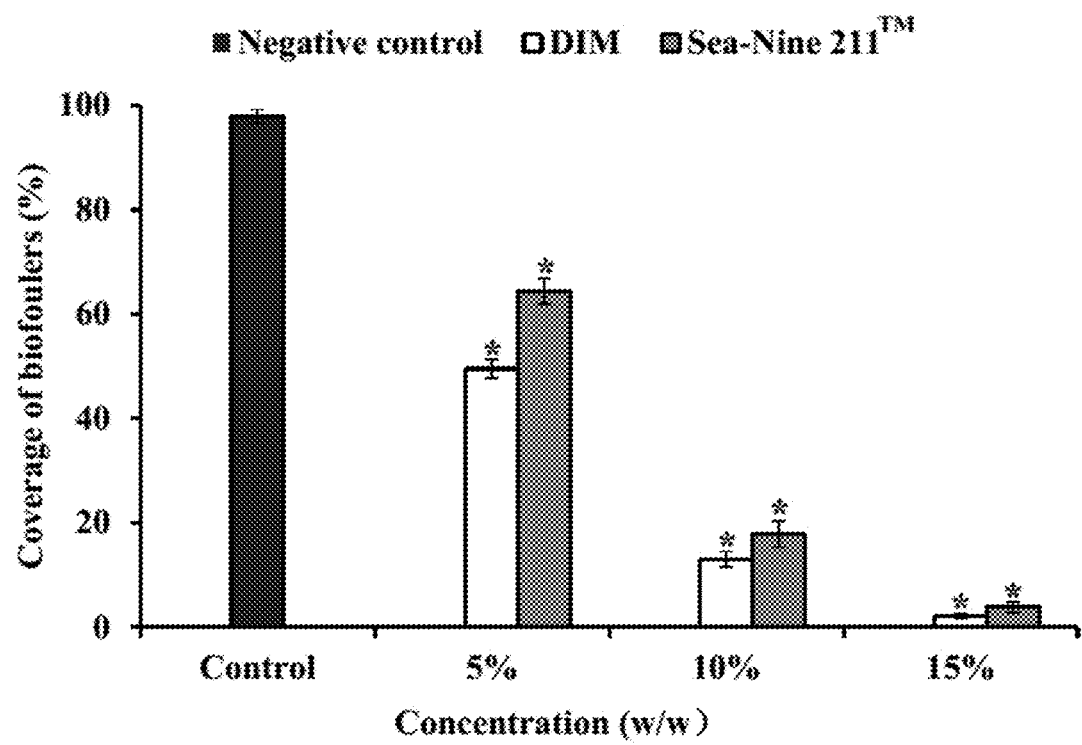

FIG. 3 shows a graph of the results of field test of compound 1 (di(1H-indol-3-yl)methane, DIM) and Sea-Nine 211™ (4,5-dichloro-2-N-octyl-3(2H)-isothiazolone, DCOIT) was conducted at Sai Kung Pier. Photographs show the surface condition of tested panels after submersion in sea water for 5 months. (A) Test panel No. 1, negative control panel coated with the basal paint; (B) No. 2, 5% (w/w) DIM (1) in base ingredients; (C) No. 3, 5% Sea-Nine 211™ in basal ingredients; (D) No. 4, 10% DIM (1) in base ingredients; (E) No. 5, 10% Sea-Nine 211™ in basal ingredients; (F) No. 6, 15% DIM (1) in base ingredients; (G) No. 7, 15% Sea-Nine 211™ in basal ingredients FIG. 4 shows the percentage (mean±SD (n=3)) of area covered by biofoulers on the testing panels in FIG. 3. Asterisks above the bars indicate significant differences from the negative control in Tukey's test (p<0.05, One-way ANOVA).

DETAILED DISCLOSURE OF THE INVENTION

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

In one aspect, the present invention provides methods of preventing or reducing settlement and/or fouling of marine fouling organisms on a surface of a submerged object, comprising:

obtaining a composition comprising one or more compounds represented by formula I:

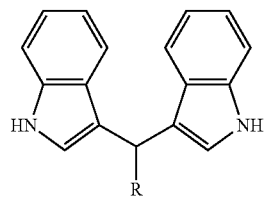

(I)

wherein R is selected from H, $CH_3$, $CHOHCH_2$, $C_8H_7N$, $COC_8H_7N$, $C_9H_6N$, Ph, Ph-4-OH, and Ph-4-OAc; and applying an effective amount of the composition to the surface, whereby settlement and/or fouling of marine fouling organisms on the surface is prevented or reduced. In preferred embodiments, the methods prevent or reduce settlement and/or fouling of marine fouling organisms while remaining non-toxic to the surrounding marine environment.

In some embodiments, the compounds comprise one or more compounds represented by formulas II-X:

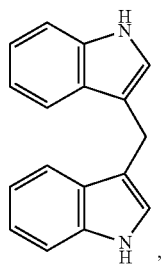

(II)

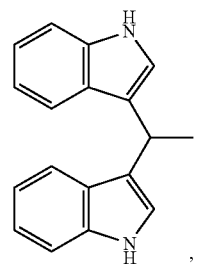

(III)

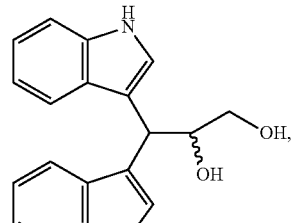

(IV)

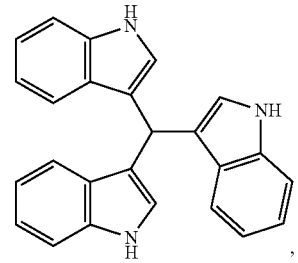

(V)

-continued

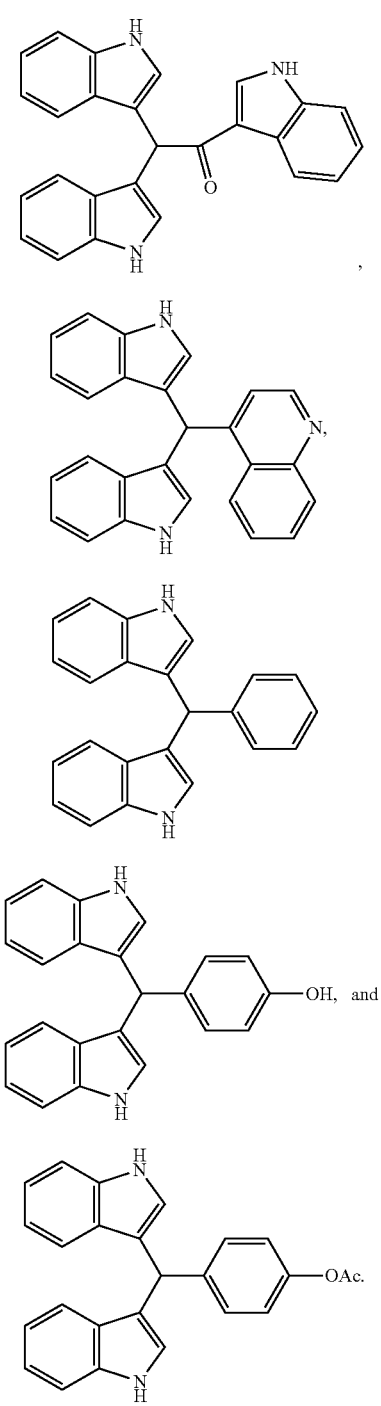

(VI), (VII), (VIII), (IX), (X)

In some embodiments, the compounds represented by formulas II-X are synthesized. In some embodiments, the one or more compounds represented by formulas II-X exist in an extract of *Pseudovibrio* sp. strain UST4-50. Such extracts can be obtained with a solvent and utilized as an extract. Solvents can include any solvent known to those skilled in the art, such as, but not limited to 70-95 vol % ethanol/water solutions, 70-90 vol % methanol/water solutions, or 50-70 vol % acetone/water solutions. In some embodiments, the compounds described herein can be utilized as a purified compound.

In some embodiments, the one or more compounds can be blended as antifouling components into film-forming components, and are therefore made into antifouling coatings which can be used to inhibit the settlement and/or fouling of marine fouling organisms on the surface of the submerged object. The antifouling coatings can be, for example, water-soluble bulk coatings, self-polishing copolymer antifouling coatings, non-adhesive coatings, low surface energy antifouling coatings, adhesive coatings, bionical antifouling coatings, and/or natural antifouling coatings. The film-forming components can include, but are not limited to, the components known in antifouling paints used for preventing marine biofouling. These film-forming components may include components as recognized by those skilled in the art, such as but not limited to, one or more hydrolysable, soluble or insoluble resins. For example, the resins can be one or more of glyptal resin, acrylic resin, chlorinated rubber resin, epoxy resin, silicone resin, polyester resin, polyurethane resin, fluoropolymer resin, and combinations thereof, as well as other resins known to those skilled in the art. The film-forming components can make up paint, such as a marine paint. In preferred embodiments, the antifouling coatings prevent or reduce settlement and/or fouling of marine fouling organisms while remaining non-toxic to the surrounding marine environment that comes in contact with a coated surface.

The content of the antifouling components in the antifouling coatings (e.g., antifouling paints) is provided at an effective amount. An "effective amount" is the content of the antifouling components in which the antifouling effect of the components is prominent under certain conditions. For example, based on the total weight of the film-forming components, the amount of the antifouling components can be up to about 5%, up to about 10%, or up to about 15% (w/w). An effective amount would be understood by those skilled in the art as an amount that is capable of inhibiting or reducing the attachment and/or growth of larvae and/or adults of fouling organisms, such as but not limited to one or more of barnacles, tubeworms, and bryozoans.

In another aspect, the present invention provides antifouling coatings, for reducing settlement and/or fouling of marine fouling organisms on a surface of a submerged object, comprising film-forming components and antifouling components; wherein the film-forming components comprise one or more resin; and wherein the antifouling components comprise one or more of the compounds represented by formula I:

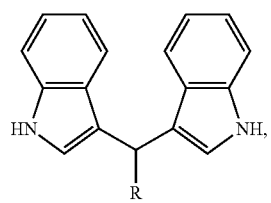

(I)

wherein R is selected from H, $CH_3$, $CHOHCH_2$, $C_8H_7N$, $COC_8H_7N$, $C_9H_6N$, Ph, Ph-4-OH, and Ph-4-OAc.

In another aspect, the present invention provides methods for preventing or reducing settlement and/or fouling of marine fouling organisms on a surface of a submerged object, comprising painting the surface of the submerged object with the antifouling coatings as provided herein.

The marine fouling organisms in which the methods and compounds of the present invention are useful against include, but are not limited to, one or more of barnacles, tubeworms, and bryozoans. In one embodiment, the compounds and antifouling coatings provided by the present invention may at least inhibit settlement of one or more of the fouling organisms. In other embodiments, the compounds and antifouling coatings provided by the present invention may at least inhibit larvae settlement of one or more of the fouling organisms.

The submerged objects that may be coated with the compounds and coatings of the present invention include any object with a surface that may be submerged in a marine (including brackish) water environment for a period of time. Such objects include, but are not limited to, a part of a ship's hull, a drain pipe, a boat propeller, a cage, an underwater dock structure, an underwater structure on offshore oil platforms, a submarine mine, a buoy, submarine cable, and coastal cooling pipes of power plants.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

The following materials and methods were used for all the methods, compounds, and compositions exemplified herein.

Bacterial strain Isolation and identification—The marine strain UST4-50 was isolated from the Red Sea. Amplification of its 16S rRNA genes and purification of the 16S PCR products were carried out according to the method of Hiraishi (1992). PCR products were sequenced by using a BigDye Terminator kit (Applied Biosystems, USA) according to the manufacturer's instructions. Phylogenetic analysis of the 16S rRNA gene sequence revealed that this microbial strain belongs to *Pseudovibrio denitrificans*.

Bacterial fermentation—The bacterium was cultured in 1 L liquid medium (containing 2 g yeast extract, 5 g tryptone, 10 g glucose, and 40 g Red Sea salts dissolved in double distilled water, pH 7.6) in 3 L multiple flasks and then incubated on a rotary shaker at 250 rpm at 30° C. for 3.5 days. A total of 50 L culture broth of *Pseudovibrio denitrificans* UST4-50 was obtained.

Isolation of secondary metabolites from UST4-50—The bacterial culture broth was centrifuged at 5000 g for 30 min to remove the cells and the supernatant was extracted three times with an equal volume of ethyl acetate (EtOAc). The combined EtOAc layer was evaporated to dryness under reduced pressure to afford crude extract, which was loaded onto a vacuum column with reversed-phase silica gel and eluted with a gradient system from water to methanol to yield 5 fractions. The fractions collected were tested for antifouling activity against larval-attachment of the barnacle *Balanus* (=*Amphibalanus*) *amphitrite* and the bryozoan *Bugula neritina*, and then the active ones were further purified on a preparative HPLC column. In total, the pure compounds 1-8 were finally accumulated.

The structure elucidation of pure metabolites derived from *Pseudovibrio denitrificans* UST4-50—The $^1$H-NMR spectra of pure compounds were recorded on a JEOL DRX 500 HZ NMR instrument at ambient temperature in deuterated dimethyl sulfoxide-$d_6$ (DMSO-$d_6$) with TMS as the internal reference. The MS spectra data of these compounds were analyzed by UPLC (Waters ACQUITY, USA) coupled with the MicroTOF-MS system (Bruker Daltonics GmbH, Bremen, German).

Larval settlement bioassay for 3,3'-diindolylmethanes (DIMs)—Adults of *B. amphitrite* were collected from the pilings of the Sai Kung Pier in Hong Kong (22° 38' N., 114° 27' E.) and the newly released nauplii of this species were reared to the cypris stage (ready to settle and metamorphose), according to Harder et al. (2001) described. Newly transformed cyprids were collected for the experiment.

Adult colonies of *B. neritina* were collected from the floating rafts at a fish farm in Yung SHU O, Hong Kong (22° 24' N., 114° 21' E.) and maintained in flow-through sweater for <7 days before use. The larvae were released under certain conditions described in Maki et al. (1989). Under the inducement of a bright artificial light for 20-30 minutes, the adult *B. neritina* placed in glass tank filled with 0.45 μm filtered seawater released their larvae, which were quickly able to attach and metamorphose. A good number of actively swimming larvae were obtained and immediately used for the anti-larval bioassay.

The experiment for evaluating inhibitory effect of the related compounds on *B. amphitrite* and *B. neritina* larvae was conducted in 24-well polystyrene plates (Nunc, Naperville, Ill., Calif., USA). A stock solution of 50 mg ml$^{-1}$ of each compound was prepared in DMSO, diluted 1000 times with fresh seawater (FSW) to 50 μg ml$^{-1}$, and further diluted by a serial 2-fold dilution to obtain test solutions of seven concentrations ranging from 25 to 0.39 μg mL$^{-1}$. Sixteen to twenty larvae were then added to each well with one milliliter of the test solution. There were three replicate wells per solution. The wells containing DMSO-FSW (v/v 1:1000) served as the negative controls while those contain Sea-Nine $^{211}$™ at the concentration of 1.90 μg mL$^{-1}$ (the EC50 value for *B. amphitrite*) and 2.50 μg mL$^{-1}$ (the EC$_{50}$ value for *B. neritina*) (Li et al., 2013) served as the positive controls. The 24-well plates were maintained in the dark for 48 h at 28° C. The number of settled larvae (attached and metamorphosed), swimming and dead larvae were counted under a dissecting microscope at 48 hr. The number of the settled larvae was expressed as a percentage of the total number of larvae per well. The mortality rate was determined as the percentage of the dead or missing larvae over the total number of larvae. Each bioassay experiment had three biological replicates and was repeated three times using three different batches of larvae.

Calculation of $EC_{50}$ and $LC_{50}$ Values—In the anti-larval settlement bioassay, the EC50 (the concentration where 50% of larvae were inhibited to settle in comparison with that in the negative control) and $LC_{50}$ (the concentration where 50% of larvae were dead in comparison with that in the negative control) values of each compound were calculated from a concentration-response curve, which was plotted according to the record of anti-larval settlement experiment. The data were analyzed by one-way analysis of variance (ANOVA) to detect significant differences in larval settlement with regard to the concentration used ($p<0.05$).

Acetylation Procedures of 4-hydroxyphenyl-3,3'-diindolylmethane (DIM-Ph-4-OH)—Acetic anhydride (0.5 ml) was added to the pyridine solution (1 ml) of compound DIM-Ph-4-OH (3 mg) in $N_2$ atmosphere. The mixture was stirred for 24 hr at room temperature (23° C.). Finally, the reaction was quenched by the addition of double distilled water (0.3 ml) and extracted with dichloromethane (DCM). The combined organic layer was washed with brine (saturated sodium chloride solution), dried over anhydrous $Na_2SO_4$, and concentrated in vacuo. The red residue was purified with silica gel column chromatography, and eluted with DCM to give the desired product DIM-Ph-4-OAc (2.8 mg, red amorphous powder, 83% yield). All the reactions were performed at room temperature (23° C.).

Reversibility tests—Cyprids were exposed and in the laboratory, recovery bioassay was designed and conducted to determine whether antifouling compounds 3,3'-diindolylmethane (DIM) and 4-hydroxyphenyl-3,3'-diindolylmethane (DIM-Ph-4-OH) had any detrimental effect on larvae. Cyprids were exposed to the test compounds at the concentrations (25.39 µM for DIM and 73.93 µM for DIM-Ph-4-OH that inhibited almost 100% larval settlement in the anti-larval settlement bioassay. After 24 hr, the treated larvae were fully rinsed with FSW for four times and transferred to new 24-well plates containing FSW only. The plates were incubated for additional 48 hr at room temperature (23° C.) in darkness. At 48 hr, the number of attached, swimming and dead cyprids were counted under a dissecting microscope. Petri dishes where the untreated cypris larvae were maintained in FSW and DMSO plus FSW 0.1% were served as the negative controls. The bioassay experiments were performed in triplicate.

Preparation of test panels—The paints with different formulas of antifouling compounds were brushed onto the sandblasted PVC panels (19 cm×14 cm×3 mm) according to the method described by Skattebol et al. (2006) and Xu et al. (2010) with minor modifications. Briefly, the plates were coated with the mixed paints containing the basal ingredients as follows: 0.4, 0.8 and 1.2 g of DIM or Sea-Nine 211™, 2.5 g of polyacrylic resin, 1.0 g of gum resin, 1.0 g of calcium carbonate, 2.0 g of titanium oxide, 0.2 g of bentonite, and 10.0 ml of xylene. After stirring the paint for 4-5 hr, it was immediately painted onto the sandblasted PVC panels. The painted plates were allowed to dry in dark. These painted plates were divided into three groups: (1) the negative control was just made of the soluble matrix paint without any antifouling agents; (2) the positive control was coated with the antifouling paints containing three concentrations (5%, 10% and 15% (w/w) respectively) of Sea-Nine 211™ in the mixed components; (3) the DIM-based panels were painted with coatings at the same concentration gradient of Sea-Nine 211™ as that of the second group. All painted plates were fixed by ropes at approximately 1.0 m below water line on the pilings supporting the Sai Kung Pier in Hong Kong (22° 38' N., 114° 27' E.). The field tests were performed in triplicate over a period of 5 months.

Calculation of Area Covered by Biofoulers—The condition of the painted surface of each panel was monitored and photographed weekly over a period of 5 months. All the images were analyzed with the ImageJ program (available as a public domain Java image processing software provided by NIH Image). Since the fouling organisms attached on the panel had different gray scale from the normal panel surface, we followed the calculation method adopted by Zhu et al. (2010) to identify the threshold between surface covered by organisms and surface uncovered. Subsequently, the total area covered by biofoulers was calculated and was then divided by the total area of the panel surface to give rise to the percent coverage of biofoulers on each panel.

Data Analysis—Data were analyzed using the SPSS statistical package. In the anti-larval settlement assay, the $EC_{50}$ for percentage of attachment and $LC_{50}$ for larval mortality were calculated by using the software Probit. Differences in all tests between treatments and controls were determined by one-way ANOVA followed by Tukey's test. Results from the one-way ANOVA were reported as means and standard deviations (SD), and considered to be significant when $p<0.05$.

Example 1

Chemical Structures and Antifouling Activities of Compounds from *Pseudovibrio denitrificans* UST4-50

Figure 1:
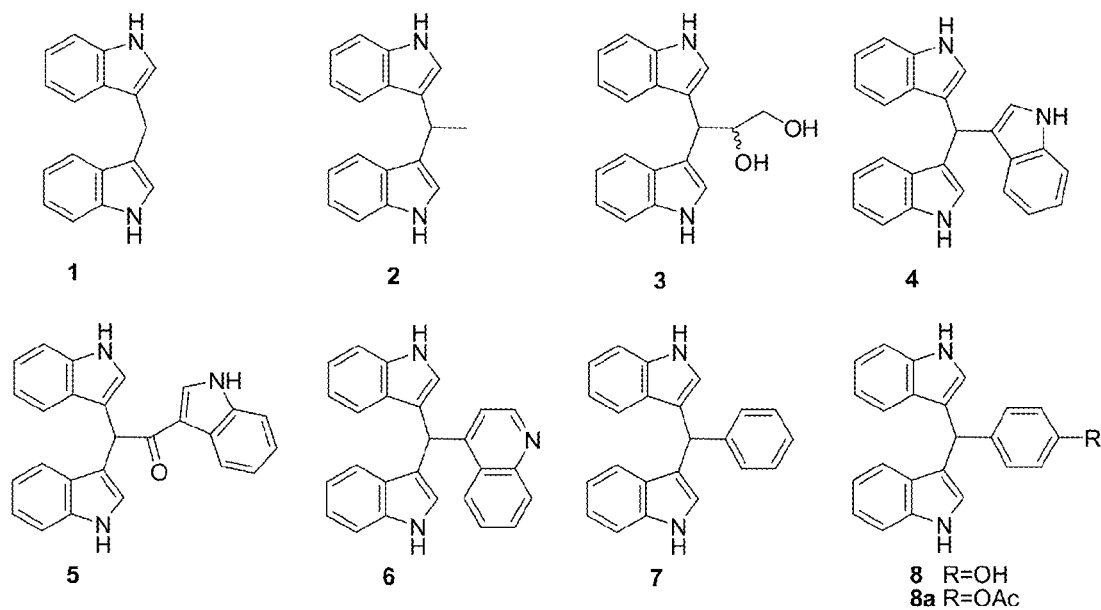
FIG. 1 illustrates the chemical structures of nine bisindole alkaloids. Compounds 1-8 were isolated from the crude extract of a bacterium *Pseudovibrio denitrificans* UST4-50 associated with an unidentified Red Sea ascidian, and the compound 8a (4-[di(1H-indol-3-yl) methyl]phenyl acetate, DIM-Ph-4-OAc) was an acetylized derivative of compound 8 (4-(di(1H-indol-3-yl)methyl)phenol, DIM-Ph-4-OH)

In this study, 50 L of *P. denitrificans* UST4-50 culture broth were exhaustively extracted by ethyl acetate (EtOAc), which yielded 10.5 g of crude extract. The major and moderate polar components of the extract were tentatively identified as indole alkaloids, based on their characteristic UV-absorbing spectra and color reaction with Ehrlich's reagent for indoles (Veluri et al., 2003). The bioassay-guided fractionation and further purification of the crude extract led to the discovery of eight known indole alkaloids (FIG. 1). In comparison with related physicochemical characteristics and NMR spectral data of chemical standard DIM (commercial DIM was purchased from Sigma Chemical, the detailed information of commercial source has been included in supplementary information) and authentic compounds previously reported in literatures (Bell at al. 1994; Veluri et al. 2003; Roy et al. 2014), the chemical structures of compounds 1-8 were determined as di(1H-indol-3-yl) methane (DIM) (1), vibrindole A (2), 3,3'-di-1H-indol-3-yl-1,2-propandiol (3), tri(1H-indol-3-yl)methane (4), 1,2,2-tri (1H-indol-3-yl) ethanone (5), arsindoline A (6), 3,3'-(phenylmethylene) bis-1H-indole (7), and 4-(di(1H-indol-3-yl)methyl) phenol (DIM-Ph-4-OH) (8) (see FIG. 1).

The chemical structures of compounds 1-8 are notable in their possession of di(1H-indol-3-yl)methylene parent nucleus. 3,3'-diindolylmethane (DIM) is a major acid condensation product of diindole-3-carbinol (I3C), a constituent of cruciferous vegetables, and was firstly reported as a natural product isolated from the North Sea bacterium *Vibrio parahaemolyticus* Bio249 (Veluri et al., 2003). In addition to the bacterium *V. parahaemolyticus* Bio249, DIM and its analogues were found in other secondary metabolites of marine γ-proteobacteria including *Vibrio parathaemolyticus* associated with the boxfish *Ostracion cubicus* (Bell et al., 1994) and *Aeromonas* sp. CB101 (Cai et al., 2010). To our best knowledge this is the first report on production of 3,3'-diindolylmethanes (DIMs) from the α-proteobacterium *Pseudovibrio* sp.

DIM and its derivatives exhibit many different biological functions. These bisindole alkaloids serve as effective chemoprevention and treatment drugs for numerous forms of cancers in vitro and in vivo (Clark and Lee 2014). DIMs target multiple components of cancer cell-cycle regulation and survival including Akt-NF kB signaling, caspase activation, cyclin-dependent kinase activities, estrogen metabolism and endoplasmic reticulum stress (Banerjee et al. 2011; Weng et al. 2008). DIM also inhibits human breast cancer cell metastases and promotes breast cancer cell differentiation by activating the aryl-hydrocarbon receptor (AhR), which was considered to have a key role in its chemopreventive effects (Hall et al. 2010). These bisindole compounds also displayed antibacterial, antioxidant, antileishmanial, anti-inflammatory activities and other functions (Kim et al. 2014; Roy et al. 2014). Ecologically, the diverse bioactivities of these metabolites might play important roles in defending the host macroorganisms against unwanted microfouling.

In the present invention, the antifouling activities of compounds 1-8 were discovered for the first time (Table 1). Except of compound 3 with two hydroxyl groups, all DIMs tested showed moderate to strong inhibitive effects on larval settlement of *B. amphitrite* with relatively low $EC_{50}$ values ranging from 6.20 μM to 1.60 μM. In comparison with the butenolide, a promising antifouling compound recently developed by our group, some of the DIMs (compounds 1, 7 and 8) showed comparable antifouling activity (Tables 1 and 2). More importantly, the $LC_{50}$ values of all these compounds were even higher than 130 μM, which was about 50 μg mL$^{-1}$. The high $LC_{50}/EC_{50}$ ratios (Clare et al. 1992) suggested that these DIMs exhibited excellent antifouling activity against *B. amphitrite* larvae without lethal effects at the effective concentrations. Therefore, DIM (1) and its analogues can be considered as non-toxic antifouling agents. Furthermore, we tested the antifouling activity of DIM (1) and DIM-Ph-4-OH (8) against larvae of the bryozoan *Bugula neritina* (a soft-fouler) and found that both compounds inhibited larval settlement with EC50 values of 2.54 μM and 1.25 μM respectively and that $LC_{50}/EC_{50}$ ratios of both compounds were high, which further confirmed that these DIMs had good antifouling activity with low toxicity.

Figure 2:
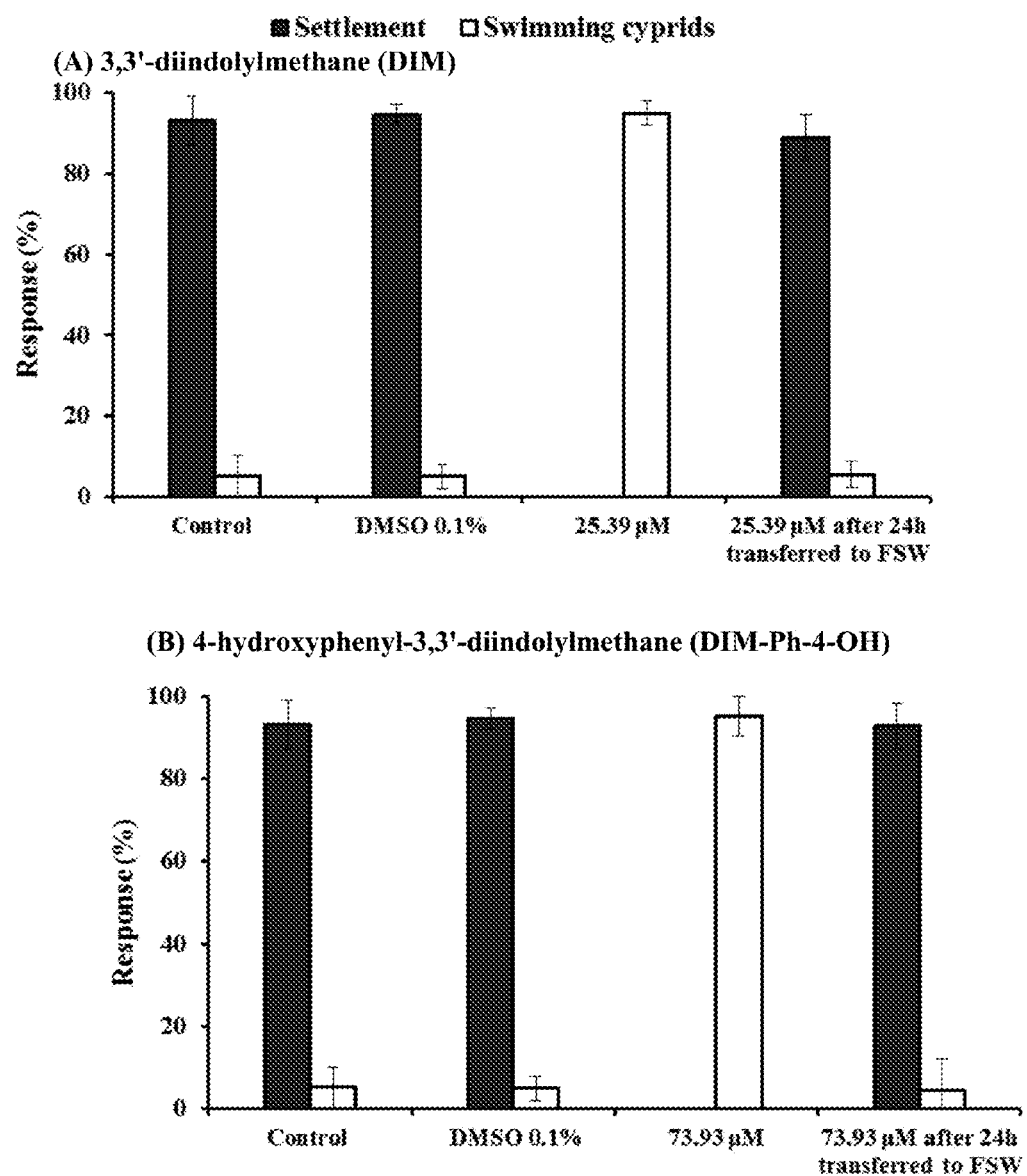
FIG. 2 shows a graph of the results of the recovery bioassay of (A) compound 1 (di(1H-indol-3-yl)methane, DIM) and (B) compound 8 (4-(di(1H-indol-3-yl)methyl) phenol, DIM-Ph-4-OH) on settlement inhibition. Cyprids were firstly exposed to the concentrations of DIM (1) (25.39

A good non-toxic antifouling compound should not kill larvae during the bioassay and upon removal of the antifouling compound, and the larvae that had been exposed to antifouling compound should be able to complete normal settlement. In order to demonstrate the non-toxic effects of DIM (1) and DIM-Ph-4-OH (8) to target marine organisms in addition to their high $LC_{50}/EC_{50}$ ratios, the recovery experiments were conducted to check whether swimming cyprids could normally attach and metamorphose in filtered seawater after being exposed to DIMs. As FIG. 2 shows, 93% of DIM (1)-treated cyprids and 95% of DIM-Ph-4-OH (8)-treated cyprids at the respective concentrations of 25.39 μM (50 μg mL$^{-1}$) and 73.93 μM (100 μg mL$^{-1}$) retained their ability of normal attachment and metamorphosis, which further confirmed the low-toxic antifouling effects of these compounds on target marine organism.

TABLE 1

Antifouling activities of di(1H-indol-3-yl)methanes (DIMs), indole and butenolide against the barnacle *Balanus* (= *Amphibalanus*) *amphitrite*.

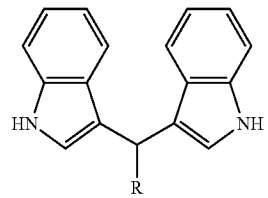

| Compounds | | *Balanus amphitrite* cypris larvae (μM) | | |
|---|---|---|---|---|
| No | R | $EC_{50}$ | $LC_{50}$ | $LC_{50}/EC_{50}$ |
| 1 | H | 3.27 ± 0.53 | >203.15 | >53 |
| 2 | $CH_3$ | 5.42 ± 0.19 | >192.21 | >34 |
| 3 | $CHOHCH_2OH$ | 18.57 ± 0.79 | >326.65 | >17 |
| 4 | $C_8H_7N$ | 5.81 ± 0.53 | >138.45 | >23 |
| 5 | $COC_8H_7N$ | 4.19 ± 0.15 | >128.44 | >30 |
| 6 | $C_9H_6N$ | 4.64 ± 0.59 | >133.99 | >26 |
| 7 | Ph | 3.57 ± 0.12 | >155.21 | >42 |
| 8 | Ph-4-OH | 1.86 ± 0.24 | >147.87 | >70 |
| 9 | Ph-4-OAc | 4.34 ± 0.32 | >131.53 | >28 |
| Indole | — | 17.51 ± 0.60 | 85.43 | 4.72 |

$EC_{50}$ refers to the concentration in which 50% of larval population was inhibited while $LC_{50}$ refers to the concentration in which 50% of the test larvae population was killed in comparison with the control.
Data = mean ± SD (n = 3), * p < 0.05; ** p < 0.01 (one-way ANOVA).

Example 2

Structure-Activity Relationships of DIMs

As Table 1 shows, all DIMs with the bisindole skeleton exhibited strong inhibitive effects on larval settlement. We were curious about the antifouling activity of structures with single indole skeleton, particularly since Kawamata et al. (2006) reported that some of halogenated gramines with single indole skeleton exhibited good antifouling activities. Therefore, we tested the settlement-inhibitory activity of the indole alone and found that indole showed only weak antifouling activity but had a relatively high toxicity ($EC_{50}$=17.50 μM, $LC_{50}/EC_{50}$=4.72, see Table 1). Furthermore, 1,1,1-tris(3-indolyl)methane (4) with three indole rings showed higher antifouling activity than indole but lower activity than DIM. The common moiety, di(1H-indol-3-yl) methylene, of DIMs may serve as an important functional group of DIMs for their antifouling activity and that their antifouling mechanism might be different from that of indole. In addition, compound 3 is the least active compound among all 8 tested compounds. Based on the differences of their structures, the two hydroxyl groups on the carbon side-chain of compound 3 might affect its antifouling activity by modifying its lipophilicity. In fact, the similar case has already been reported in the antifouling activities of furanone compounds (Xu et al. 2010). It is possible that compound 3 cannot enter cells easily by passive diffusion, and consequently, can lead to the negative expression of its antifouling activity at reduced concentration compared to less lipophilic compounds (Siddiqui et al. 1999). Among all the analogues tested, DIM-Ph-4-OH (8) was the best antifoulant against *B. amphitrite* larval settlement. In comparison with the other nine compounds, the presence of the phenolic hydroxyl substituent at the Ph-C1''' substantially enhanced antifouling activity of this compound. In order to clarify the importance of phenolic hydroxyl group for antifouling activity, we conducted an acetylized modification of the phenolic hydroxyl group in DIM-Ph-4-OH (8) and checked its antifouling activity against barnacle cyprids. As expected, the antifouling activity of DIM-Ph-4-OAc (8a) was not as high as that of DIM-Ph-4-OH (8) (Table 1). Similarly, the compound DIM-Ph (7), which only possesses a benzene ring linked to the C1 position, also had weaker anti-larval settlement activity than DIM-Ph-4-OH (8). The inhibitive activity of DIMs against *B. amphitrite* larval settlement was significantly enhanced when a phenolic hydroxyl group presents at the Ph-C1''' of DIM-C1. The same trend of antifouling activity of DIM (1), DIM-Ph-4-OH (8), and DIM-Ph-4-OAc (8a) was observed when they were tested with *B. neritina* (see Table 2), further suggesting that phenolic hydroxyl group might have enhanced antifouling activity of DIMs.

DIM-Ph-4-OH (8) showed not only the best antifouling activity among all the DIMs tested but also lower toxicity to larvae than DIM as indicated by the higher recovery rate of larvae after being exposed to antifouling compounds. Therefore, DIM-Ph-4-OH (8) might have the less ecological disturbance in future application. Here, we chose to use compound DIM (1) for the field bioassay in our follow-up field test after considering current synthetic costs of these compounds.

TABLE 2

Antifouling activities of compounds 1 (di(1H-indol-3-yl)methane, DIM), 8 (4-(di(1H-indol-3-yl)methyl)phenol, DIM-Ph-4-OH), 8a (4-[di(1H-indol-3-yl)methyl]phenyl acetate, DIM-Ph-4-OAc), indole and butenolide the bryozoan *Bugula neritina*.

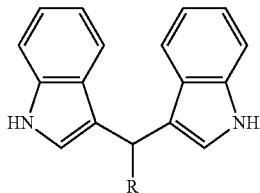

| Compounds | | *Bugula neritina* larvae (μM) | | |
|---|---|---|---|---|
| No | R | $EC_{50}$ | $LC_{50}$ | $LC_{50}/EC_{50}$ |
| 1 | H | 2.54 ± 0.50 | >203.15 | >67 |
| 8 | Ph-4-OH | 1.25 ± 0.47 | >147.87 | >86 |
| 9 | Ph-4-OAc | 4.50 ± 0.42 | >131.53 | >27 |

Both compound 1 (3,3'-diindolylmethane, DIM) and 8 (4-hydroxyphenyl-3,3'-diindolylmethane, $EC_{50}$ refers to the concentration in which 50% of larval population was prevented while $LC_{50}$ refers to the concentration in which 50% of the test larvae population was killed in comparison with the control.
Data = mean ± SD (n = 3), * p < 0.05; ** P < 0.01 (one-way ANOVA).

Example 3

Field Tests of DIM

Extending laboratory bioassays of antifouling compounds to field testing is a critical step in the development of natural product-based antifoulants. In the present study, DIM (1) was incorporated into basal paints for field testing, and the commercial antifouling biocide Sea-Nine 211™ was chosen as a reference to assess the relevant antifouling performance of DIM (1). FIG. 4 shows the different extents of biofouling on tested panels submerged in seawater in the field for 5 months. The effect of DIM (1) in preventing larval settlement of fouling organisms was in a concentration-dependent manner in field condition, which was well documented in laboratory bioassay. As shown in FIGS. 3 and 4, the surface of the negative control panels (without any biocides) was almost 100% covered by barnacle adults. In a striking contrast, there were few marine organisms observed on the surface of 10% and 15% treated PVC panels (see FIGS. 3 and 4). At these two concentrations, the excellent antifouling activity of DIM (1) was comparable to Sea-Nine 211™ during the period of field test. In addition, excellent antifouling activity of the testing paints at these two concentrations lasted for several more months (similar to that of Sea-Nine 211™). Moreover, the results of our field experiment suggested that DIM (1) might be useful for preventing settlements of various marine organisms in natural environment. The results from the field tests show that DIM (1) is an excellent candidate for antifouling ingredient in marine paints. Furthermore, Burgess et al. (2003) and Cahill et al. (2013) reported that the leaching rate and the retained amount of antifouling agents, which obviously affected antifouling potency, could be controlled by the addition of copolymer, meaning that the lifespan of the antifouling performance of DIM can be improved by controlling the content of resin in basal paints in future practical application. In addition, the preliminary hydrolysis experiment in natural seawater suggests that DIM was quickly degraded (with ~90% degraded after 4 d). On the contrary, no obvious degradation was observed for Sea-Nine 211™ after 4 d incubation. The rapid degradation together with the excellent antifouling activity and lower toxicity of DIM highlight its ideal application in the antifouling coating industry.

DISCUSSION

The present invention provides a group of compounds sharing a 3,3'-diindolylmethylene moiety that possess strong antifouling activities. In addition, the compounds DIM and DIM-Ph-4-OH showed non-cytotoxic properties to primary mouse neurons, suggesting that the antifouling activity of the DIMs may be exerted in a non-toxic mechanism at their effective concentrations, rather than through the severe cytotoxicity reported previously. The field test also demonstrated the capability of DIM to deter the settlement of a broad-spectrum of marine fouling organisms over 3 months or longer. In summary, many properties of DIMs, such as their relatively simple chemical structures, excellent antifouling activities, negligible toxicities on target organisms, make them ideal environmentally-friendly antifouling agents to be incorporated in marine coatings.

REFERENCES

Banerjee, S., Kong, D., Wang, Z., Bao, B., Hillman, G. G., Sarkar, F. H., 2011. Attenuation of multi-targeted proliferation-linked signaling by 3,3'-diindolylmethane (DIM) from bench to clinic. Muta. Res. 728, 47-66.

Bell, R., Carmeli, S., R., Sar, N., 1994. Vibrindole A, a metabolite of the marine bacterium, *Vibrio parahaemolyticus*, isolated from the toxic mucus of the boxfish *Ostracion cubicus*. J. Nat. Prod. 57, 1587-1590.

Burgess J. G., Boyd K., Armstrong E., Jiang Z., Yan L., Berggren M., May U., Pisacana T., Granmo A., Adams D., 2003. The development of a marine natural product-based antifouling paint. Biofouling 19, 197-205.

Cahill, P. L., Heasman, K., Jeffs, A., Kuhajek, J., 2013. Laboratory assessment of the AF potential of a soluble-matrix paint laced with the natural compound polygodial. Biofouling 29, 967-975.

Cai, S. X., Li, D. H., Zhu, T. J., Wang, F. P., Xiao, X., Gu, Q. Q., 2010. Two new indole alkaloids from the marine-derived bacterium *Aeromonas* sp. CB 101. Helv. Chim. Acta. 93, 791-795.

Callow, M. E., Callow, J. E., 2002. Marine biofouling: a sticky problem. Biologist (London) 49, 10-14.

Clare, A. S., Rittschof, D., Gerhart, D. J., Maki, J. S., 1992. Molecular approaches to nontoxic antifouling. J. Invert. Reprod. Dev. 22, 67-76.

Clark, R., Lee, S. H., 2014. Synergistic anti-cancer effects of capsaicin and 3,3'-diindolylmethane in human colorectal cancer, involvement of NF-kB and p53. FASEB J. 29, 644.

Davidson, I. C., Brown, C. W., Sytsma, M. D., Ruiz, G. M., 2009. The role of containerships as transfer mechanisms of marine biofouling species. Biofouling 25, 645-655.

Dobretsov, S., Dahms, H. U., Qian, P. Y., 2006. Inhibition of biofouling by marine microorganisms and their metabolites. Biofouling 22, 43-54.

Fusetani, N., 2004. Biofouling and antifouling. Nat. Prod. Rep. 21, 94-104.

Fusetani, N., 2011. Antifouling marine natural products. Nat. Prod. Rep. 28, 400-410.

Hall, J. M., Barhoover, M. A., Kazmin, D., McDonnell, D. P., Greenlee, W. F., Thomas, R. S., 2010. Activation of the aryl-hydrocarbon receptor inhibits invasive and metastatic features of human breast cancer cells and promotes breast cancer cell differtiation. Mol. Endocrinol. 24, 359-369.

Harder, T. N., Thiyagarajan, V., Qian, P. Y., 2001. Effect of cyprid age on the settlement of Balanus amphitrite Darwin in response to natural biofilms. Biofouling 17, 211-219.

Hiraishi, A., 1992. Direct automated sequencing of 16S rDNA amplified by polymerase chain-reaction from bacterial cultures without DNA purification. Lett. Appl. Microbiol. 15, 210-213.

Kawamata M., Kon-ya K., Miki W., 2006. 5, 6-Dichloro-1-methylgramine, a Non-Toxic Antifoulant Derived, in: Fusetani, N. and Clare A. S. (Eds.), Antifouling compounds. Springer, Berlin, 2006, pp. 125-140.

Kim, H. W., Kim, J., Kim, J., Lee, S., Choi, B.-R., Han, J.-S., Lee, K. W., Lee, H. J., 2014. 3,3'-Diindolylmethane inhibits lipopolysaccharide-induced microglial hyperactivation and attenuates brain inflammation. Toxicol. Sci. 137, 158-167.

Kwong, T. F., Miao, L., Li, X., Qian, P. Y., 2006. Novel antifouling and antimicrobial compound from a marine-derived fungus Ampelomyces sp. Mar. Biotechnol. 8, 634-640.

Li, Y. X., Wu, H. X., Xu, Y., Shao, C. L., Wang, C. Y., Qian, P. Y., 2013. Antifouling activity of secondary metabolites isolated from Chinese marine organisms. Mar. Biotechnol. 15, 552-558.

Maki, J. S., Rittschof, D., Schmidt, A. R. Snyder, A. G., Mitchell, R., 1989. Factors controlling attachment of bryozoan larvae: a comparison of bacterial films and unfilmed surfaces. Biol. Bull. 177, 295-302.

Plouguerne, E., Ioannou, E., Georgantea, P., Vagias, C., Roussis, V., Hellio, C., Kraffe, E., Stiger-Pouvreau, V., 2010. Anti-microfouling activity of lipidic metabolites from the invasive brown alga Sargassum muticum (Yendo) Fensholt. Mar. Biotechol. 12, 52-61. Qian, P. Y., Lau, S. C. K., Dahms, H. U., Dobretsov, S., Harder, T., 2007. Marine biofilms as mediators of colonization by marine macroorganisms: implications for antifouling and aquaculture. Mar. Biotechnol. 9, 399-410

Qian, P. Y., Xu, Y., Fusetani, N., 2010. Natural products as antifouling compounds: recent progress and future perspectives. Biofouling 26, 223-234. Qian, P. Y., LI, Z. R., Xu, Y., Li, Y. X., Fusetani, N. 2015. Mini-review: Marine natural products and their synthetic analogues as antifouling compounds: 2009-2014. Biofouling 31, 101-122.

Roy, S., Gajbhiye, R., Mandal, M., Pal, C., Meyyapan, A., Mukherjee, J., Jaisankar, P., 2014. Synthesis and antibacterial evaluation of 3,3'-diindolylmethane derivatives. Med. Chem. Res. 23, 1371-1377. Siddiqui A Q, Ballatore C, McGuigan C, De Clercq E, Balzarini J (1999) The presence of substituents on the aryl moiety of the aryl phosphor ramidate derivative of d4T enhances anti-HIV efficacy in cell culture: a structure-activity relationship. J. Med. Chem. 42, 393-399.

Sievers, M., Fitridge, I., Dempster, T., Keough, M. J., 2013. Biofouling leads to reduced shell growth and flesh weight in the cultured mussel Mytilis galloprovincialis. Biofouling 29, 97-107.

Sipkema, D., Franssen, M. C. R., Osinga, R., Tramper, J., Wijffels, R. H., 2005. Marine sponges as pharmacy. Mar. Biotechnol. 7, 142-162 Skattebol, L., Nilsen, N. O., Stenstrom, Y., Andreassen, P., Willemsen, P., 2006. The antifouling activity of some juvenoids on three species of acon barnacle, Balanus. Pest Manag. Sci. 62, 610-616.

Tsukamoto, S., Kato, H., Hirota, H., Fusetani, N., 1997. Antifouling terpenes and steroids against barnacle larvae from marine sponges. Biofouling 11, 283-291.

Veluri, R., Oka, I., Wagner-Dobler, I., Laatsch, H., 2003. New indole alkaloids from the north sea bacterium Vibrio parahaemolyticus Bio249. J. Nat. Prod. 66, 1520-1523. Weng, J. R., Tsai, C. H. , Kulp, S. K., Chen, C. S., 2008. Indole-3-carbinol as a chemopreventive and anti-cancer agent. Cancer Lett. 262, 153-163.

Wieczorek, S. K., Todd, C. D., 1997. Inhibition and facilitation of bryozoan and ascidian settlement by natural multispecies biofilms: effects of film age and the roles of active and passive larval attachment. Mar. Biol. 128, 463-473

Xu, Y., He, H., Schulz, S., Liu, X., Fusetani, N., Xiong, H., Xiao, X., Qian, P. Y., 2010. Potent antifouling compounds produced by marine Streptomyces. Bioresour. Technol. 101, 1331-1336. Zhu, X. Y., Bai R. B., Wee, K. H., Liu, C. K., Tang, S. L., 2010. Membrane surfaces immobilized with ionic or reduced silver and their anti-biofouling performances. J. Membrane Sci. 363, 278-286.

We claim:

1. A method of preventing or reducing settlement and/or fouling of marine fouling organisms on a surface of a submerged object, comprising:

obtaining a composition comprising one or more compounds represented by formula I:

(I)

wherein R is selected from H, $CH_3$, $CHOHCH_2OH$, $C_8H_6N$, $COC_8H_6N$, $C_9H_6N$, Ph, Ph-4-OH, and Ph-4-OAc; and applying an effective amount of the composition to the surface, whereby settlement and/or fouling of marine fouling organisms on the surface is prevented or reduced.

2. The method of claim 1, wherein the compounds comprise one or more compounds represented by formulas II-X:

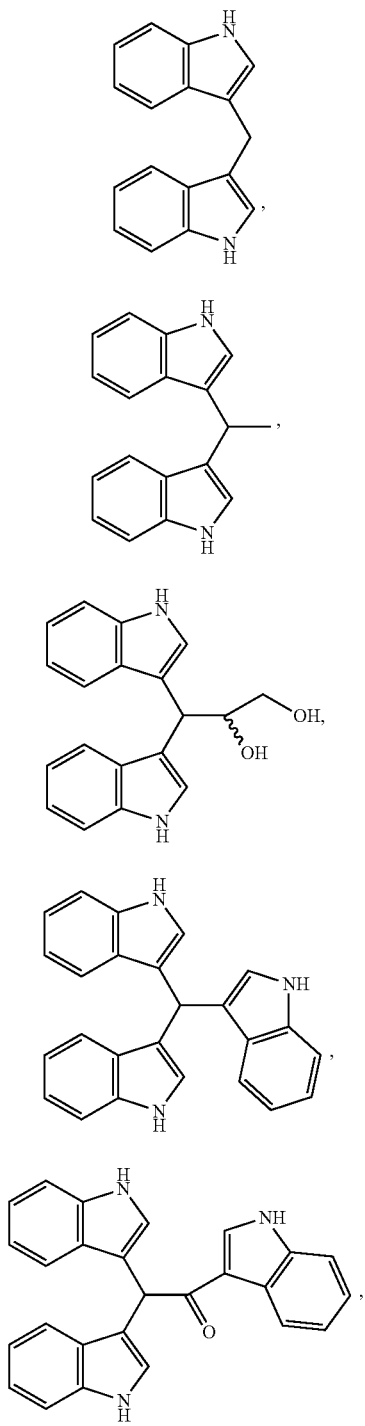

(II)

(III)

(IV)

(V)

(VI)

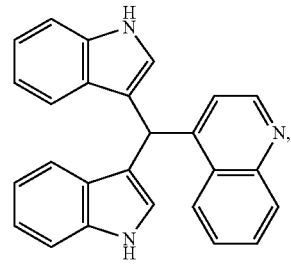

(VII)

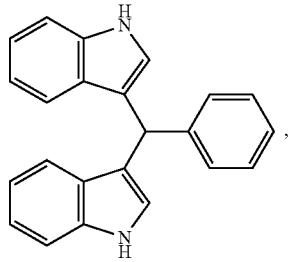

(VIII)

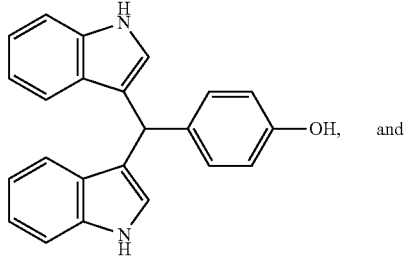

(IX)

and

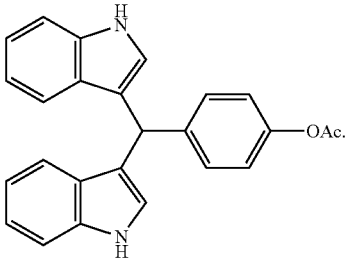

(X)

3. The method of claim 1, wherein the one or more compounds are blended as antifouling components into film-forming components, and are therefore made into an antifouling coating which can be used to inhibit the settlement and/or fouling of marine fouling organisms on the surface of the submerged object.

4. The method of claim 3, wherein the antifouling coating is in the form of paint.

5. The method of claim 1, wherein the marine fouling organisms are *Bugula* or *Balanus*.

6. The method of claim 1, wherein the marine fouling organisms are barnacles or bryozoans.

7. The method of claim 1, wherein the marine fouling organisms are *Bugula neritina* or *Balanus amphirite cypris*.

* * * * *